United States Patent [19]

Anderson, III et al.

[11] Patent Number: Plant 5,837

[45] Date of Patent: Dec. 23, 1986

[54] PISTACHIO TREE

[76] Inventors: Henry P. Anderson, III; Kenneth L. Puryear, both of Pioneer Nursery, 800 N. Chester, Bakersfield, Calif. 93308

[21] Appl. No.: 696,247

[22] Filed: Jan. 29, 1985

[51] Int. Cl.[4] ..... A01H 5/03

[52] U.S. Cl. ..... Plt./30

[58] Field of Search ..... Plt./30

*Primary Examiner*—Robert E. Bagwill

[57] ABSTRACT

This invention relates to a new and distinct variety of pistachio tree primarily identified by its rounded upright growth habit, abundant foliage and its production of female flowers and seed.

6 Drawing Figures

The present invention relates to a new and distinct variety of pistachio tree, the variety being primarily characterized, as to novelty, by vigorous, rounded, upright (vase shape) growth habit and the abundant production of female (pistilate) flowers and seeds.

The variety is further characterized by abundant foliage of medium green color and the production of seeds useful for planting to grow understocks upon which commercial nut bearing pistachio varieties may be budded or grafted.

A tree which is vigorous, of rounded upright growth habit with semi-glossy to matte foliage with pointed leaflets; the flowers being borne in slender clusters or bunches similar to grapes.

A tree which has a normal height of 15 to 20 feet when mature and a spread about equal to height or less.

A plant which grows and flowers satisfactorily in any well drained soil and which, when pollenized with a selected male pistachio variety, produces seeds useful for growing nursery understocks upon which to bud of graft commercial nut bearing varieties.

Variety name: Identification number—PN-83-F.

The present variety of pistachio was originated by us at our orchards located at Delano, Kern County, Calif., under conditions of careful control and observation, as a selection from numerous seedlings of *Pistachio atlantica* (species) being grown and tested at the time in our search for improved pistachio understocks on which to bud or graft commercial nut bearing varieties.

Subsequent to origination of the variety we successfully asexually reproduced it at our orchard/nursery, located as aforesaid, by budding and by grafting, the reproductions having run true in all respects.

The color photographs illustrate the variety, including (A) young trees in seed orchard (bearing age), (B) branch of current season's growth showing (juvenile) foliage, (C) cluster of immature fruit (nuts) showing type of fruiting cluster, (D) shows seeds for comparison (1) hybrid of present variety; (2) seeds of pistachio Var.PN-17-F X Var. PN-46-M, (3) *P. atlantica* (species).

Further, photos (E) and (F) show young nursery trees (same age) for comparison. FIG. (E) seed planted February, 1983: left — new hybrid seedlings grown from PN-83-F (present variety) X PN-46-M (Pat. 4994); center — hybrid seedlings from PN-17-F X PN-46-M (known commercially as Pioneer Gold TM); right — *P. atlantica* (species) commonly used as an understock.

FIG. (F) shows seedlings (same order — all same age) with soil removed showing the superior root system and larger top of plant (left) grown from hybrid seed (PN-83-F X PN-46-M). NOTE: darker solid area (root zone) in photo is remains of Jiffy — 7 (peat pots) in which seeds were planted.

Referring now specifically to the new and distinct variety of pistachio tree, the following is a detailed description thereof in outline; all major color plate identifications, if any, being by reference to The British Colour Council Horticultural Colour Chart, except where common terms of color definition are employed.

Flowers borne in elongated clusters of many individual female flowers, similar to a bunch of grapes.

Quantity of bloom: abundant.

Buds: very small in size and brownish color.

Bloom size when fully open—very small, with flowers opening at random over a period of several days to assure as complete pollenation as possible.

Flowering time (at Delano, Calif.)—generally the latter part of February to about March 15th, the flowering time coinciding well with the pollenizer variety PN-46-M.

Seeds resulting from the cross PN-83-F (the present variety) X PN-46-M produce hybrid seedling understocks of great uniformity, rapid growth and disease resistance. These seedling understocks are apparently much less susceptable to verticillium wilt disease, particularly SS4 and T1 (cotton strain) which has caused extensive loss of commercial orchard trees budded or grafted on other commonly used pistachio understocks. These hybrid seedlings also appear to be more resistant to cold and wet soils than other commonly used understocks.

Color:

*Flower cluster.*—From tree in seed orchard, Delano, Calif.

*Main stem of bunch and smaller side branches.*—Are medium green, sometimes shaded or tinted brownish.

*Flowers.*—Pinkish.

Reproductive organs: All female.

*Pistil.*—Small, short.

*Stigma.*—Well formed.

*Fruit (nuts).*—Borne in loose elongated clusters: small.

Foliage:

*Leaves.*—Compound of nine or more (sometimes less, as indicated in FIGS. (B) and (C).).

*Leaflets.*—Medium small, leathery, semi-glossy to matte. Shape: long narrow (lanceolate); apex acute; base acute but less so than apex. Color: medium to dark green, near Spinach Green 0960; new growth — normal (medium) green often tinted reddish, especially young leaves on tips of shoots. Ribs (center) of leaves and center rib of leaflets usually slightly lighter green color than rest leaf surface.

*Length of leaves (including petiole and leaflets).*—May average about 6 inches or more; to end of midrib, 4½ inches or more.

Growth:

*Habit.*—Upright when young, becoming much branched and upright to spreading when mature. Tree may or may not have central leader plus several main branches. These main branches support numerous lesser limbs and branches to form a dense symetrical crown or head.

*Color.*—Main branches and limbs — to brownish.

The new variety of pistachio tree as herein described may vary in slight detail due to climatic, soil and cultural conditions under which the variety may be grown, the present description being of the variety as grown at Delano, Calif.

The following is claimed:

1. A new and distinct variety of pistachio tree (identified as PN-83-F) characterized by a mature tree of rounded upright shape, having several main branches; rapid growth, abundant, leathery foliage, ease of propagation by budding or grafting; and further characterized by the abundant production of female flowers, in clusters, followed by seeds which are especially desirable for planting (when pollenized by the male variety, identified as PN-46-M), said hybrid seeds producing a fast growing, disease resistant tree of value for use as understock upon which to bud or graft commercial nut bearing varieties of pistachio such as 'Kerman'.

* * * * *

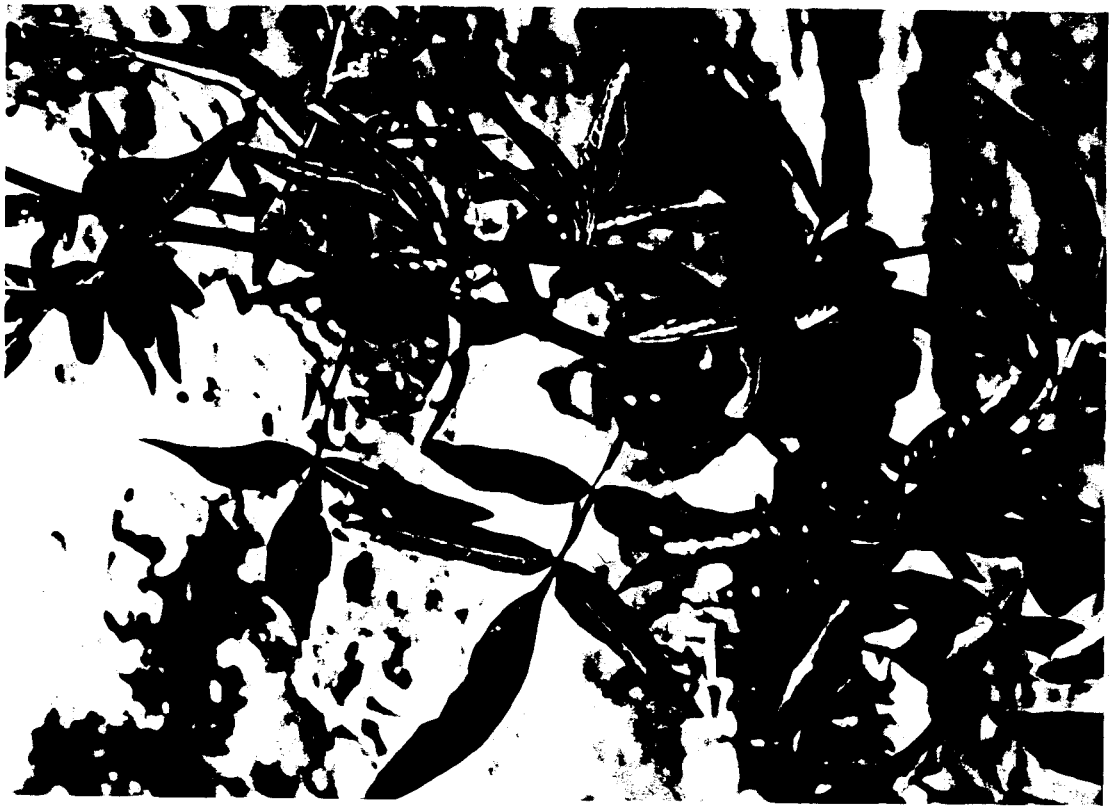
-B-
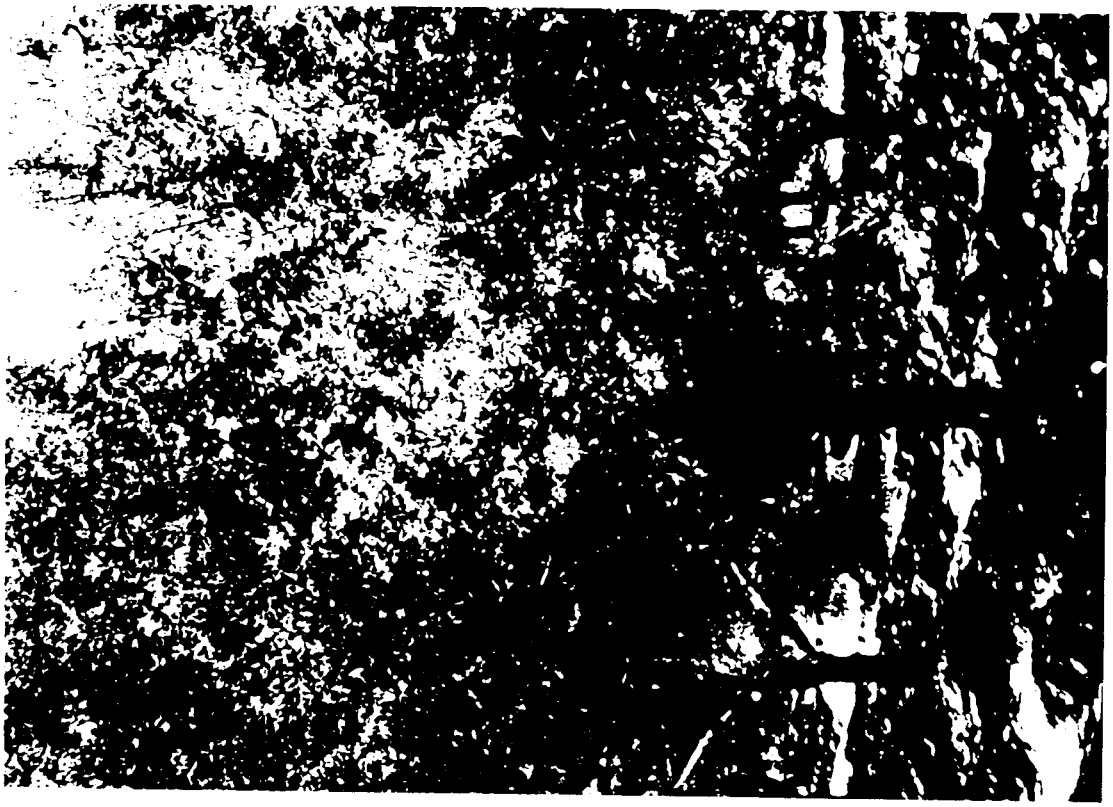
-A-

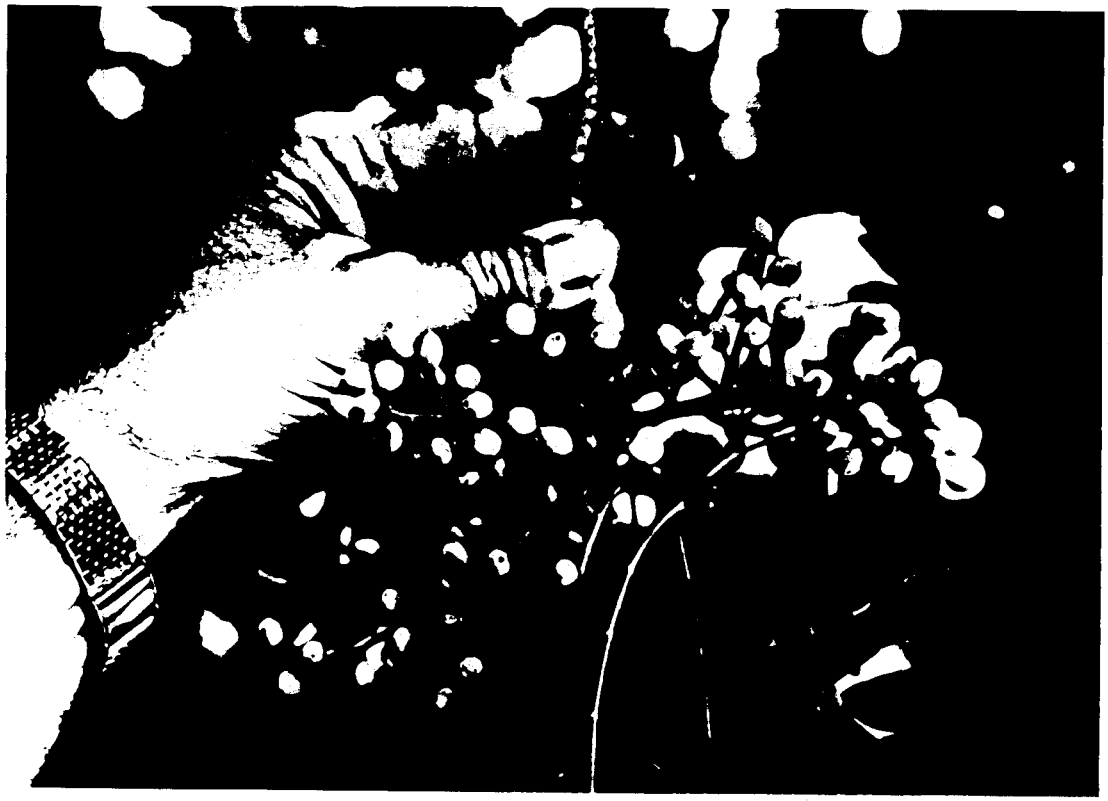
-C-
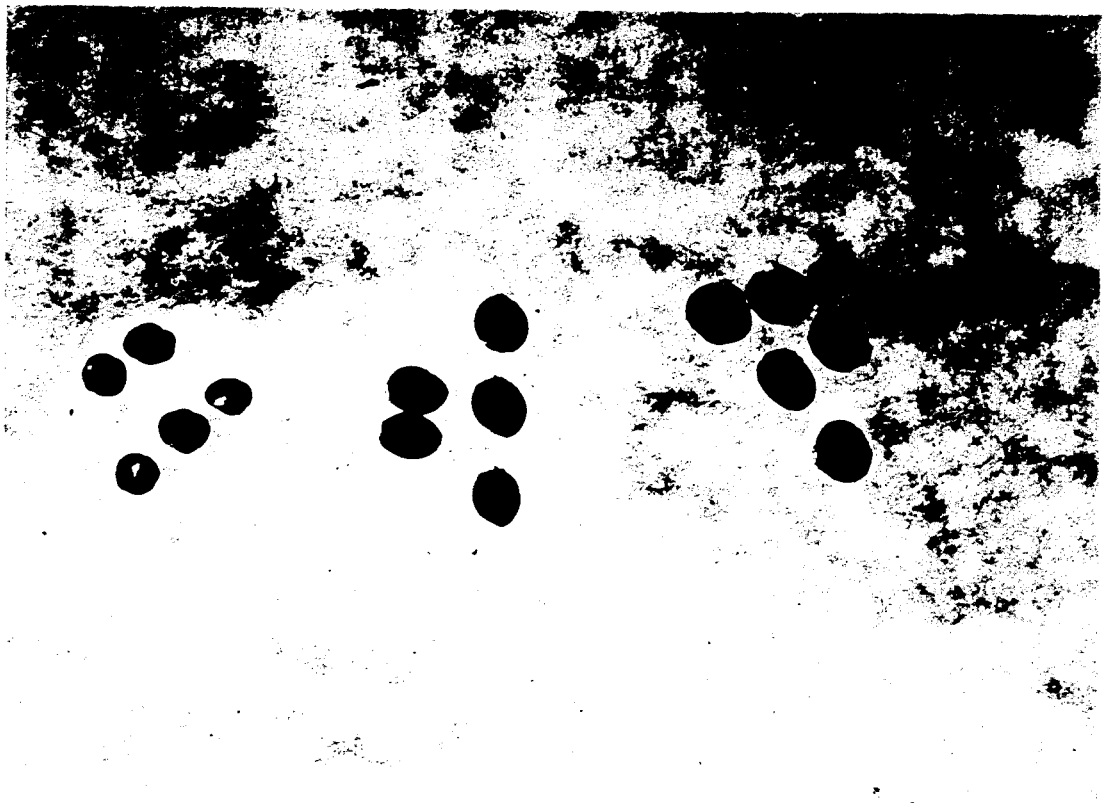
-D-

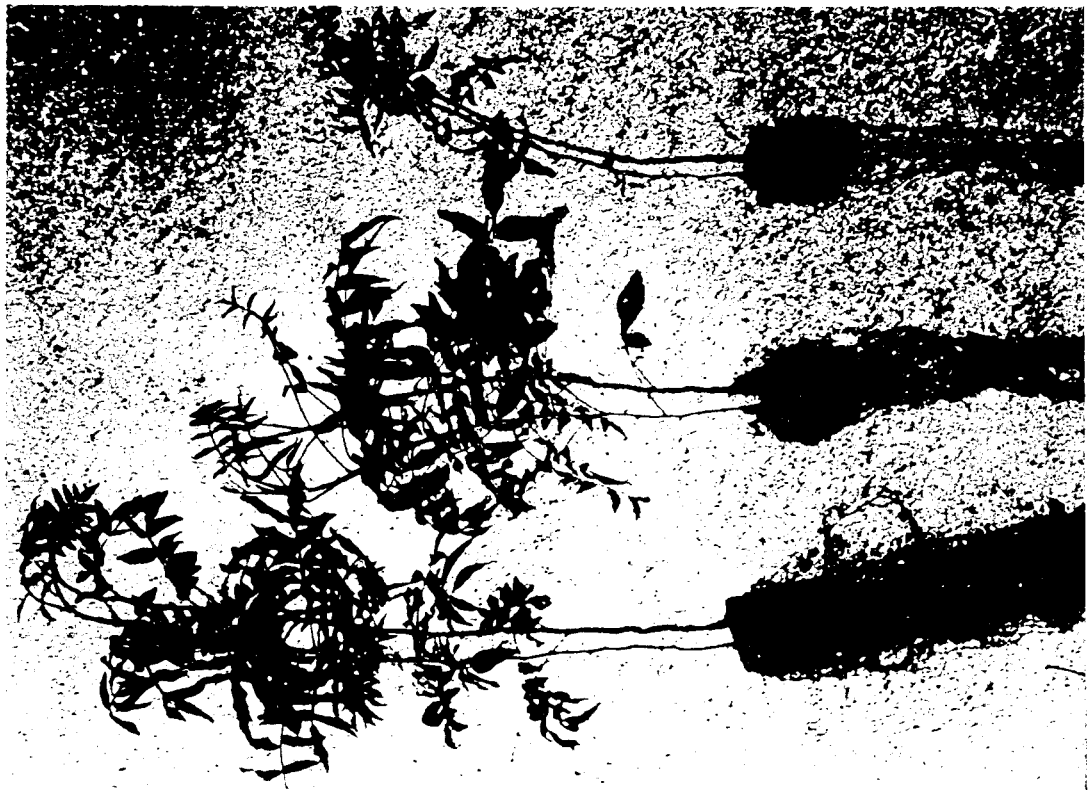
– F –
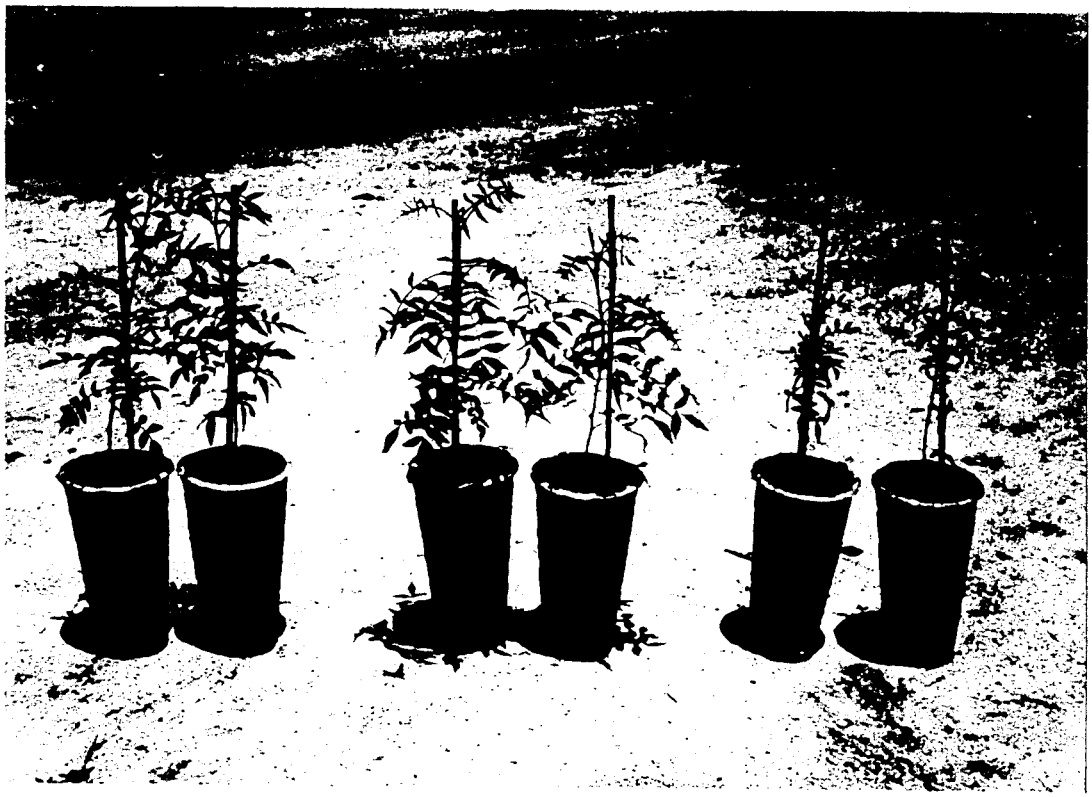
– E –